United States Patent [19]

Pardridge

[11] Patent Number: 5,130,129
[45] Date of Patent: * Jul. 14, 1992

[54] METHOD FOR ENHANCING ANTIBODY TRANSPORT THROUGH CAPILLARY BARRIERS

[75] Inventor: William M. Pardridge, Pacific Palisades, Calif.

[73] Assignee: The Regents of the University of California, Berkeley, Calif.

[*] Notice: The portion of the term of this patent subsequent to Apr. 2, 2008 has been disclaimed.

[21] Appl. No.: 488,993

[22] Filed: Mar. 6, 1990

[51] Int. Cl.$^5$ .................... A61K 39/00; A61K 43/00; C07K 15/28; C07K 3/08

[52] U.S. Cl. .................... 424/85.8; 424/85.91; 530/387.1; 530/388.1; 530/402; 530/391.3; 530/391.7; 530/863

[58] Field of Search ............... 424/1.1, 9, 85.8, 85.91; 530/387, 388, 389, 402

[56] References Cited

U.S. PATENT DOCUMENTS

| | | | |
|---|---|---|---|
| 4,118,379 | 10/1978 | Schmidtberger | 530/390 |
| 4,219,335 | 8/1980 | Ebersole | 436/518 |
| 4,417,967 | 11/1983 | Ledley | 204/182.1 |
| 4,444,744 | 4/1984 | Goldenberg | 424/1.1 |
| 4,454,106 | 6/1984 | Gansow et al. | 424/1.1 |
| 4,478,815 | 10/1984 | Burchiel et al. | 424/1.1 |
| 4,585,651 | 4/1986 | Beck et al. | 424/88 |
| 4,624,846 | 11/1986 | Goldenberg | 424/1.1 |
| 4,699,784 | 10/1987 | Shih et al. | 424/85.91 |
| 4,732,763 | 3/1988 | Beck et al. | 424/433 |
| 4,732,974 | 3/1988 | Nicolotti et al. | 530/390 |
| 4,735,210 | 4/1988 | Goldenberg | 424/9 |
| 4,741,900 | 5/1988 | Alvarez et al. | 424/85 |
| 4,756,907 | 7/1988 | Beck et al. | 424/85 |
| 4,758,421 | 7/1988 | Goodwin et al. | 424/1.1 |
| 4,859,449 | 8/1989 | Mattes | 424/9 |
| 4,863,713 | 9/1989 | Goodwin et al. | 424/1.1 |
| 5,004,697 | 4/1991 | Pardridge | 530/391 |

OTHER PUBLICATIONS

W. M. Pardridge et al., *J. of Pharmacology and Experimental Therapeutics* 255:893-899 (1990).

E. M. Renkin, *Microvascular Research* 15: 123-135 (1978).

W. M. Pardridge et al., *J. of Pharmacology and Experimental Therapeutics* 251: 821-826 (1989).

Griffin and Giffels, *J. Clin. Invest.* 70: 289-295, 1982.

Pardridge et al., *Biochemical and Biophysical Research Communications* 146: 307-313, 1987.

Conjugation of Poly-L-Lysine to Albumin and Horseradish Peroxidase: a Novel Method of Enhancing the Cellular Uptake of Proteins. Shen, W. C. et al., Apr. 1978, *Proc. Natl. Adac. Sci. USA* 75:1872-1876.

Blood-Brain Barrier Transport of Cationized Immunoglobulin G: Enhanced Delivery Compared to Native Protein. Triguero et al., Jun. 1989, *Proc. Natl. Acad. Sci. USA* 86:4761-4765.

Effect of Cationized Antibodies in Preformed Immune Complexes on Deposition and Persistence in Renal Flomeruli. Gauthier, V. J. et al., Sep. 1982, *J. Exp. Med.* 156:766-777.

Effects of Polycations on Vascular Permeability in the Rat, a Proposed Role for Charge Sites. Vehaskari et al., Apr. 1984, *J. Clin. Invest.* 73:1053-1061.

Tissue Uptake of Immunoglobulin G is Greatly Enhanced Following Cationization of the Protein. Pardridge et al., Abstract: Western AFCR Oncology, *Clinical Research*, vol. 38, No. 1, 1990, p. 133A.

*Primary Examiner*—Robert A. Wax
*Assistant Examiner*—Stephen Walsh
*Attorney, Agent, or Firm*—Poms, Smith, Lande & Rose

[57] ABSTRACT

A method for increasing the transcytosis of an antibody across the microvascular barrier and into the interstitial fluid of organs is disclosed. The method consists of cationizing the antibody with a cationizing agent to increase the isoelectric point of the antibody by between about 1 to about 7 to produce a cationized antibody having an isoelectric point which is less than about 11.5. The increased rate of transport across the microvascular barrier of organs makes such cationized antibodies useful for both therapeutic and diagnostic purposes.

13 Claims, 3 Drawing Sheets

METHOD FOR ENHANCING ANTIBODY TRANSPORT THROUGH CAPILLARY BARRIERS this invention was made with United States Government support under Contract No. DAMD1787-C-7137 awarded by the Department of the Army. The United States Government has certain rights in this invention.

BACKGROUND OF THE INVENTION

1. Field of the Invention

The present invention relates generally to the use of antibodies for treatment and diagnosis of diseases, most notably tumors and cancerous lesions. More particularly it relates to the modification and use of cationized antibodies for transport through capillary barriers into the interstitial fluid of organs.

2. Description of Related Art

Antibodies in general, and especially monoclonal antibodies, are widely used in diagnostic tests as a means for detecting the presence of specific antigens and in the treatment of diseases associated with a specific antigen. More particularly, antibodies have been used as targeting vehicles for radioisotopes, magnetic resonance imaging agents, toxins and cytotoxic drugs, especially in the diagnosis and treatment of cancer, tumors, and certain infectious diseases.

Enzyme linked immunoassay and radioimmunoassay are common diagnostic techniques which utilize antibodies as targeting vehicles and detect antigens in vitro. Antigens may also be detected in vivo by administering radio labelled or paramagnetic labelled antibodies to a living subject followed by the external detection of the radio labelled antibody sequestered by a particular organ bearing the respective antigen.

One of the limitations in using antibodies as targeting vehicles in either the in vivo treatment or diagnosis of cancer and infectious diseases has been the inability to obtain effective concentrations of the targeting antibody at the target site. The low antibody dose at the site is largely due to poor antibody uptake by the tumor or infected site. The poor uptake is due to the microvascular or endothelial barrier which is present in most organs. This endothelial barrier has pores which are too small to allow for rapid organ uptake of circulating antibodies. Also the small size of the aqueous pores in the walls of the vessels which perfuse organs greatly restricts antibody transport from the vessels into the organ.

Transport across the endothelial barrier is a particular problem for large plasma proteins, such as antibodies that have molecular weights in excess of 150,000 Daltons. These antibodies are excluded or cross the microvascular barrier only very slowly. Not only does the size of these large antibodies restrict their transport across the endothelial barrier, but, their electrical charges also present transport problems. More specifically, the molecules on the surface of capillaries are anionically charged and, therefore, present an electrical barrier to the neutral or slightly negatively charged antibodies.

Another limitation to an optimum concentration of targeting antibody at the target organ site is the higher permeability of the liver and spleen vascular barrier. The liver and spleen do not exclude the transport of large molecules to the same degree as other organs. Consequently, these two organs will preferentially remove administered antibodies from the blood leaving only a small concentration for therapeutic or diagnostic delivery to other organs.

Since most of the radioisotopes or complexes used in targeting systems are somewhat toxic and dose limiting, merely increasing the dose of the antibody with the expectation that more will become available to the organ of interest is not a practical solution.

Strategies have been developed to administer effective amounts of antibodies by an invasive regional route to the location of the tumor or diseased area. This avoids a high concentration of a potentially toxic agent in the blood. For systemic administration, however, it is necessary to use methods which control or enhance the blood clearance of the targeted antibodies. Such techniques aid in avoiding toxic blood levels of radioisotopes or other therapeutic agents, but still require large doses of the antibody because of their restricted transport across capillary barriers.

Accordingly there presently is a need to provide an improved method for the diagnosis and treatment of cancer and infectious diseases which are responsive to antibodies used as target vehicles. Further, there is a need to provide improved methods for delivering effective amounts of antibodies to organ tissue without sustaining toxic amounts of the antibody target vehicle in the blood. There is also a need to provide improved means for transporting antibodies across the microvascular barrier of organs and into the interstitial pores of organs.

SUMMARY OF THE INVENTION

It is one objective of the invention to provide chemically modified yet active antibodies for delivery to organ tissue in effective amounts for therapeutic or diagnostic applications. It is another objective to effectively deliver the chemically modified antibodies without maintaining toxic levels of the antibody target vehicle in the blood. Accordingly, the present invention provides a method for increasing the transcytosis rate of an antibody across the microvascular barrier and into the interstitial fluid of organs. The invention is based upon the discovery that cationized antibodies have increased rates of delivery across organ vascular beds when compared with the transcytosis of antibodies which are not cationized.

The effectiveness of antibodies for both diagnostic and therapeutic purposes is increased by cationizing the antibodies to provide cationized antibodies having elevated isoelectric points (pI). These antibodies carry a net positive charge and have been found to cross microvascular barriers at rates which are much higher than the transcytosis rates for negatively charged or neutral antibodies which typically have isoelectric points in the range of ph 5 to 7. Isoelectric points for the cationized antibodies will vary depending upon the particular organ or organs to which the antibody is targeted. Generally, however, it is desirable to raise the isoelectric point of the antibody by from about 2 to about 6 ph units. The resulting modified antibody preferably has an isoelectric point in the range of from about 8 to about 11 ph units.

The cationized antibodies in accordance with the present invention are prepared by treating a given monoclonal or polyclonal antibody with a cationization agent such as hexamethylenediamine. The amine cationization agent replaces surface carboxyl groups on the antibody with a more basic group, such as a primary amine group in the case of hexamethylenediamine and related amine compounds. The amount of cationization agent and reaction conditions are controlled so that the resulting cationized antibody has the desired isoelectric point of between from about 8 to about 11 ph units.

It is known that antibodies retain nearly 90% of their antigen binding properties following cationation. Thus, the chemical process of cationization does not destroy the innate biologic properties of the antibody. If preferred, however, the immunoreactive sites may be blocked prior to the cationizing process by reacting the antibody with an excess of the appropriate antigen. These blocked immunoreactive sites are unreactive during the subsequent cationization steps. The antigens are then decoupled from the cationized antibodies after the cationization step to thereby reactivate the blocked immunoreactive sites.

The cationization and utilization of antibodies in accordance with the present invention is useful whenever it is necessary to introduce an antibody into the interstitial fluid of an organ. Both therapeutic and diagnostic uses for antibodies are contemplated. Diagnostic uses include targeting a cationized antibody carrying a radionuclide or a paramagnetic label to a specific organ containing the antigen for that antibody. Once the antibody and antigen are complexed, subsequent diagnostic techniques for the radionuclide or the paramagnetic label may be used to detect the antigen. Therapeutic uses include targeting drugs to specific organs containing cancerous or diseased tissue. Such therapeutic utility contemplates using cationized antibodies which are antibodies for the antigen of interest as the carrying vehicle for the drug.

The above discussed and many other features and attendant advantages of the present invention will become apparent as the invention becomes better understood by reference to the following detailed description.

DETAILED DESCRIPTION OF THE INVENTION

Figure 1:
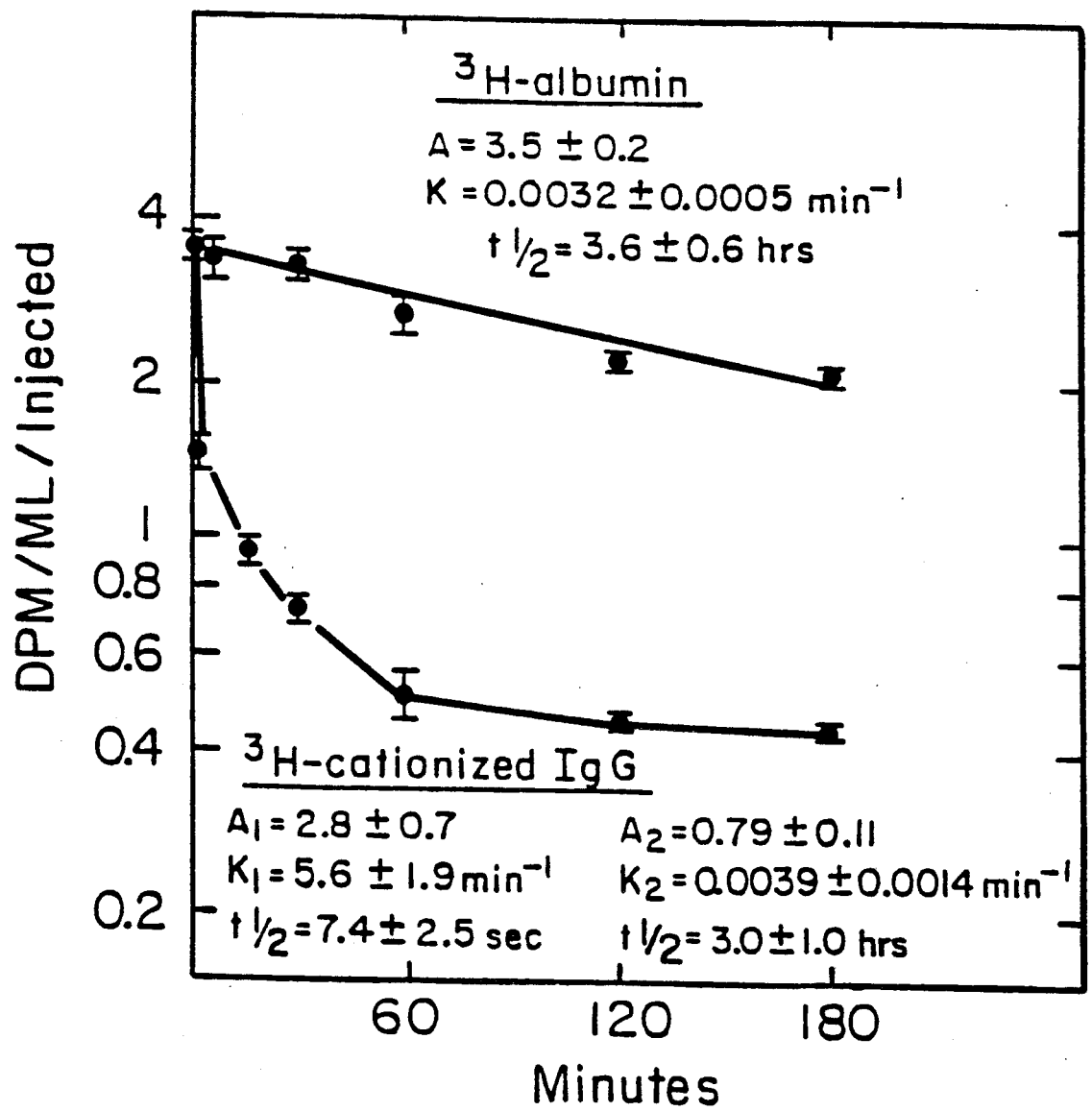
FIG. 1 is a plot of serum radioactivity (DPM/mL/% injected) of [$^3$H]-native albumin or [$^3$H]-cationized IgG versus time after a single intravenous injection of the isotope in the anesthetized rat.

The publications and other references which will be referred to in this detailed description are hereby incorporated by reference. For convenience, the reference materials are numerically referenced and grouped in the bibliography which is located at the end of the detailed description.

The present invention involves the transport of antibodies through the microvascular barrier of non-central nervous system tissues and organs. The invention has wide application to any antibody which is useful as a targeting vehicle in diagnosing or treating cancers, tumors, or diseased tissue. Antibodies in general do not readily cross capillary barriers and enter the interstitial fluid area of organs. To the degree that antibodies do cross capillary barriers their movement is very slow. Thus, when antibodies are administered for the purpose of treating or diagnosing diseased tissue associated with specific organs, the antibody dose at the infected site is too low.

The vascular beds of most organs have a net negative charge. These charged sites are attributed to the presence of negatively charged molecules on the surface of capillary walls. It is believed that these negatively charged surfaces also provide an added electrical barrier to the neutral or slightly negative charge associated with antibodies.

In addition, the size of a molecule is important in determining the ability of that molecule to cross capillary walls. Since antibodies have relatively high molecular weights their capillary permeation rate is much slower than that for similar molecules with a smaller size. In the case of IgG the molecular weight is in the region of 150,000 Daltons. For IgM it is on the order of 1,000,000 Daltons. Antibodies having lower molecular weights are transported at higher rates, but these are still well below the desired rates for therapeutic and diagnostic applications. In accordance with the present invention the transport rate of all antibodies is increased. For very large antibodies, e.g. IgM, the present invention provides a method for their therapeutic and diagnostic utility which has not been available.

This invention is based upon the discovery that the uptake or transport of antibodies across the microvascular barrier of organs can be increased by cationizing the antibodies to form cationized antibodies having an isoelectric point of between about 8 and about 11 ph units. Antibodies are proteins which have both positive and negative charges with the net charge depending upon the pH of the antibody solution. The pH at which the positive and negative charges are equal is called the "isoelectric point" (pI).

Antibodies with a relatively high pI (>- ph 7.5) have a net positive charge at normal physiological pH's of about 7.4. The higher the pI, the greater the positive charge. Conversely, antibodies with pI less than neutral have a net negative charge at normal physiological pH's. Techniques for measuring the pI of a given antibody or protein are well known and generally involve isoelectric focusing according to conventional electrophoresis procedure. As previously mentioned, most antibodies have an isoelectric point of between about pH 5 to 7.

The slightly acidic to neutral isoelectric points characteristic of most antibodies is attributed to the carboxy functionalities on the antibody. The present invention involves reacting a diamine with the carboxy groups of the antibody. One amine group of the diamine reacts with a carboxy group of the antibody to form an amide bond. The second amine functionality associated with the diamine cationization reagent provides the antibody with a basic group which raises the isoelectric point. A sufficient amount of the cationizing diamine is utilized to form a cationized antibody with the desired isoelectric point.

Cationization of the antibody can be carried out according to any of the known procedures for reacting carboxy groups on proteins to provide functionalities which give the protein high isoelectric points. Preferred cationization agents are diamine compounds such as hexamethylenediamine. Hexamethylenediamine is the most preferred cationization agent because it is widely available and the techniques for its use in cationizing proteins are well known. The amount of cationizing agent and the conditions for reaction with the antibody can be varied so long as the final cationized antibody has an isoelectric point within the desired range.

In accordance with the present invention, the higher the isoelectric point of the antibody the greater the degree of uptake by organ tissues. Thus, in general, higher isoelectric points are preferred. However, antibodies with isoelectric points in excess of about pH 11.5 are known to form aggregates. In addition to being non-therapeutic and non-useful for diagnostic purposes, the aggregates will cause toxic responses when administered. Accordingly, when choosing the appropriate isoelectric point, consideration must be given to the possibility of antibody aggregate formation at high diamine substitutions or high isoelectric point.

Another consideration in choosing the isoelectric point for the cationized antibody is the specific organ to be targeted. The microvessels which perfuse the organ contain surface anionic charges with each organ having a characteristic anionic charge density. It is believed that the positively charged cationized antibodies permeate the electrical barrier caused by the net positive charge on the microvessel surface. For monoclonal antibodies that are directed against organs perfused by vessels with a paucity of anionic charges, it is necessary to markedly increase the cationization of these antibodies relative to antibodies that are targeted toward organs perfused by capillaries with a high degree of anionic charges on the surface of the microvessels.

The above mentioned characteristics of cationized antibodies and organ vascular beds are the factors which are considered in accordance with the present invention when establishing the degree of cationization of an antibody that is necessary to enhance its organ uptake. The first factor is the isoelectric point of the antibody. If the antibody happens to be neutral or even slightly positively charged, the degree of cationization that is necessary may not be as high as that necessary in the case of a monoclonal antibody with a net negative charge. The second factor is the degree to which the targeted organ is perfused by microvessels and the anionic charge density. By varying the resulting isoelectric point of the cationized antibody, an organ specific compound can be prepared. The third factor to consider is the isoelectric point at which the cationized antibody forms an antibody aggregate. Since aggregate formation is undesirable, the isoelectric point must be less than that at which the aggregates form. The pI of the antibody may be raised between 1 to 7 pH units in accordance with the present invention provided that aggregates are not formed. For antibodies having a neutral pI, cationization will be limited to raising the pI only 1 to 4 ph units. The increase in pI for neutral antibodies directed to organs having relatively high anionic charge such as kidney or lung will be less than for organs such as intestines, which have lower anionic charges. For example, when targeting the kidney, the pI increase for a neutral antibody will be in the range of pH 1 to 3. In contrast, when targeting the intestines, the cationization should be increased to provide a pI which is 2 to 4 pH units higher than that of the neutral antibody.

For acidic antibodies, the pI should be increased from 5 to 7 pH units. Again, the specific preferred increase will depend upon the organ being targeted. The amount of increase in pI can be easily determined experimentally for each organ and each antibody.

The particular antibodies which can be used are virtually unlimited, provided that they have some use in connection with diagnosing or treating cancer, tumors, or diseased tissue. Monoclonal antibodies are preferred because of their increased diagnostic or therapeutic potential. Monoclonal antibodies which are organ specific for specific antigens are of particular importance. The invention has application to antibodies with molecular weights greater than 20,000 Daltons. Typical antibodies which can be cationized for organ transcytosis include antibodies to carcinoembryonic antigen (CEA) which can be useful for imaging or treatment of colon cancer (1) or a monoclonal antibodies to T-lymphocyte receptors which are useful in the imaging or detection of cancers of lymphoid tissue such as lymphoma (2).

Additionally, monoclonal antibodies to a surface antigen on melanoma cells may be useful in the treatment or imaging of malignant melanoma, a skin cancer (3). Any of a number of antibodies to surface antigens specific for lung cancer are suitable for use in the treatment and diagnosis of lung cancer (4). Monoclonal antibodies to surface antigens peculiar to human prostrate tissue may be useful in the imaging or treatment of prostate cancer (5). Further, monoclonal antibodies to surface proteins or antigens on human breast cancer, kidney cancer, esophageal cancer, and pancreatic cancer are particularly suitable for chemical modification and use in the treatment or diagnosis of cancer (6), (7), (8), (9).

Since monoclonal antibodies and other large proteins have difficulty in traversing the vascular barrier in colon, skin, lymph tissue, lung, prostate, breast tissue, kidney, esophagus, and pancreas, the cationization of any of these specific monoclonal antibodies in accordance with the present invention allows for marked increase in the uptake of these organ- specific monoclonal antibodies by their respective organs.

Antibodies to any of the above mentioned antigens may be tagged with a specific tracer for diagnostic purposes or a specific drug for therapeutic purposes and cationized to an isoelectric point which is selected for the specific antibody and the specific organ. The cationization agent is preferentially hexamethylenediamine and the isoelectric point is generally from about pH 8 to about 11. The amount that the isoelectric point for an antibody must be raised can be determined experimentally by first establishing the point at which aggregates form and then reducing the pI depending upon the particular organ being targeted.

The resulting tagged or drug carrying cationized antibody may be utilized as a specific organ targeted vehicle. Accordingly, it can be administered intravenously to the patient using a suitable pharmaceutically acceptable carrier solution. The tagged cationized antibody will cross the microvascular bed of the specific organ in sufficient quantities to effectively treat the cancer or detect the antigen of interest. Additionally, because of the enhanced uptake by the specific organ, dangerously high levels of the tagged antibody in the blood are avoided. When radionuclides are utilized in conjunction with cationized antibodies there is a reduced background level due to the enhanced contrast between the target and background areas. Detection of radionuclide bound cationized antibody is accomplished by conventional radionuclide scanning techniques.

Although hexamethylenediamine is the preferred compound for use in cationizing antibodies, other cationizing agents are possible. For example, ethylene diamine, N,N-dimethyl-1,3-propanediamine, or polylysine may be used. Cationization is preferably catalyzed by carboxy activation using N-ethyl,N (3-dimethylaminopropyl carbodiimidehydrochloride (EDAC) using the method described by Hoare and Koshland.(10)

It is known that cationizing antibodies does not significantly reduce their antigen binding properties. If desired however, the antibody may be pre-bound to the antigen of interest prior to cationization. This prebinding with the antigen effectively blocks the immunoreactive sites on the antibody and prevents them from reacting during the cationization process. After cationization is complete and the isoelectric point has been raised to the desired level, the cationized antibody is treated to unbind the antigen from the antibody. The unbinding is accomplished according to well known procedures where the antibody-antigen complex is treated with an acid to break the antibody-antigen bond. The antibody is then recovered by column chromatography or other conventional separation and recovery techniques.

As an example of practice, bovine IgG was cationized and the pharmacokinetics of its uptake by several organs in both rat and monkey were tested. Bovine serum albumin was used as a test control for comparison.

EXAMPLE 1

Clearance of [$^3$H]-cationized IqG and [$^{125}$I]BSA in primate

Bovine immunoglobulin G (IgG) having an initial isoelectric point of 5-7 was cationized to an isoelectric point > 10.7 as determined by polyacrylamide gel isoelectric focusing (11). The cationized IgG was monomeric as determined by sodium dodecylsulfate polyacrylamide gel electrophoresis (SDS-PAGE). Native bovine serum albumin (BSA) and cationized IgG were iodinated to a specific activity of 13 and 21 μCi/microgram, respectively, with [$^{125}$I]-iodine and chloramine T. (11 and 12) The radiolabeled protein was separated from unreacted iodine by Sephadex G25 gel filtration after passage over two 0.7×28 cm columns in series. Cationized IgG and native BSA were tritiated to a specific activity of 0.14 and 0.4 μCi/microgram, respectively, with [$^3$H]-sodium borohydride.

An 0.5 mL aliquot of physiologic buffer (10 mM Hepes, pH =7.4, 141 mM NaCl, 4 mM KCl, 2.8 mM CaCl$_2$, 1 mM MgSO$_4$, 1 mM Na H$_2$PO$_4$, and 10 mM D-glucose) containing 5 μCi of [$^{125}$I]-cationized IgG plus 50 μCi of [$^3$H]-BSA or 10 μCi of [$^3$H]-cationized IgG was rapidly injected into a femoral vein of anesthetized rats. At 0.5, 5, 30, 60, 120, and 180 minutes after the injection, the animal was quickly laparotomized and 5 mL of arterial blood was withdrawn from the descending aorta. An 0.5 mL aliquot was removed for liquid scintillation counting and trichloroacetic acid (TCA) precipitability measurements. The remaining blood was allowed to clot and the serum was separated and stored at −20 degrees C. for subsequent use in vitro studies.

The following organs were extirpated and weighed: brain, heart, liver, spleen, testis, small intestine, skeletal muscle, fat, kidney, and lung. The tissues and blood samples were solubilized in soluene 350 and prepared for [$^{125}$I], [$^3$H]double isotope liquid scintillation spectrometry.

The blood [$^3$H]and [$^{125}$I]radioactivities were normalized to DPM/mL as a percent of injected dose and these data fitted to a biexponential function. The volume of distribution (V$_D$) of the labeled protein in brain or other organs was determined from the ratio of DPM/Gm tissue divided by the integrated DPM/mL blood over the time period of the experiment. Only arterial blood which was trichloroacetic acid precipitated was counted for [$^3$H]and [$^{125}$I].

Table is a table of percent trichloroacetic acid precipitable serum [$^{125}$I]and [$^3$H]-cationized immunoglobulin G (cIgG) measured at different time intervals after a single intravenous injection in rats. The results indicate that substantially all the radio labelled material is recovered.

TABLE 1

| Trichloroacetic Acid (TCA) Precipitability of Serum [$^{125}$I]- or [$^3$H]-Cationized Immunoglobulin G (cIgG) After a Single Intravenous Injection in Rats | | |
|---|---|---|
| Time (min) | % TCA Precipitable | |
|  | [$^{125}$I]-cIgG | [$^3$H]cIgG |
| 0.25 | 99.4 ± 0.1 | 97.0 ± 0.6 |
| 5 | 99.3 ± 0.1 | 98.3 ± 0.4 |
| 30 | 98.9 ± 0.3 | 97.8 ± 0.2 |
| 60 | 97.8 ± 0.3 | 92.2 ± 1.2 |
| 120 | 97.0 ± 1.0 | 91.4 ± 0.9 |
| 180 | 97.7 ± 0.1 | 88.9 ± 1.6 |

Mean ± S.E. (n = 3).

Figure 2:
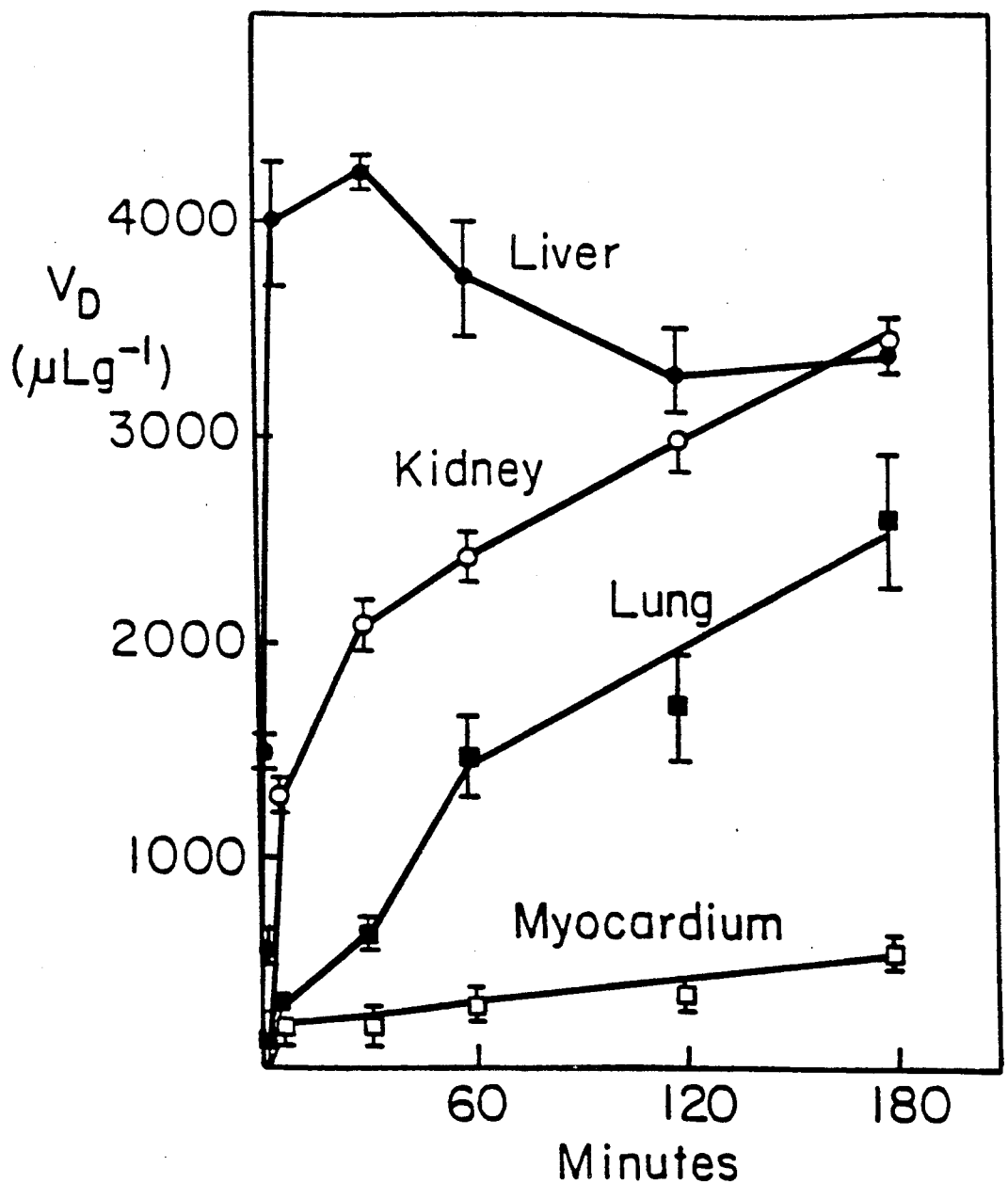
FIG. 2 is a plot of the volume of distribution ($V_o$) of [$^3$H]-cationized IgG for liver, kidney, lung, and myocardium versus the time after single intravenous injection of the isotope in anesthetized rats.

The volume of distribution (V$_D$) of [$^3$H]-cationized IgG in kidney, lung, or myocardium rose linearly with the duration of the three hour period of observation following the single intravenous injection of isotope as shown in FIG. 2. Similarly, the organ V$_D$ values for [$^3$H]-cationized IgG in brain, intestines, skeletal muscle, or fat increased linearly during the three hour observation period (data not shown). In contrast, the volume of distribution of [$^3$H]-cationized IgG in liver (FIG. 2) or spleen (data not shown) reached a maximal value within five minutes after the intravenous injection and subsequent values actually declined from this maximal volume of distribution. The volume of distribution of [$^3$H]-cationized IgG in testis peaked at 60 minutes, and this value remained constant between 60 and 180 minutes after injection. Table 2 provides the volume of distribution of [$^3$H]-cationized IgG, [$^{125}$I]-cationized IgG, and [$^3$H]-native bovine serum albumin (BSA) for the ten organs measured at a single time point of 180 minutes after single intravenous injection. Table 2 illustrates the enhanced uptake of cationized immuoglobulin G as compared to native bovine serum albumin. The ratio of transport of [$^3$H]-captionized IgG to [$^3$H]-native bovine serum albumin ranged from 1.0 (testis) to 17.9 (spleen). However, these ratios refer only to the 180 minute time point and it is projected that in organs such as kidney, brain, lung, intestine, skeletel muscle, heart, or fat the ratio of cationized IgG to native serum protein will rise appreciably beyond the values shown in Table 2 at time points later than 180 minutes after administration.

TABLE 2

| Integrated Volume of Distribution (V$_D$) of [$^3$H]-Native Bovine Serum Albumin (BSA), [$^{125}$I]-Cationized Immunoglobulin G (cIgG), and [$^3$H]-cIgG 180 Minutes After a Single Intravenous Injection in Rats | | | | |
|---|---|---|---|---|
|  | V$_D$ (μLg$^{-1}$) | | | [$^3$H]-cIgG V$_D$ |
|  | [$^3$H]-BSA | [$^{125}$I]-cIgG | [$^3$H]-cIgG | [$^3$H]-BSA V$_D$ |
| Spleen | 196 ± 30 | 951 ± 79 | 3498 ± 454 | 17.9 |
| Liver | 251 ± 8 | 1005 ± 35 | 3392 ± 143 | 13.5 |
| Kidney | 272 ± 8 | 605 ± 35 | 3380 ± 198 | 12.4 |
| Brain | 16 ± 1 | 29 ± 2 | 118 ± 8 | 7.4 |
| Lung | 360 ± 11 | 462 ± 8 | 2611 ± 264 | 7.2 |
| Intestine | 125 ± 13 | 259 ± 56 | 660 ± 19 | 5.3 |

TABLE 2-continued

Integrated Volume of Distribution ($V_D$) of [$^3$H]-Native Bovine Serum Albumin (BSA), [$^{125}$I]-Cationized Immunoglobulin G (cIgG), and [$^3$H]-cIgG 180 Minutes After a Single Intravenous Injection in Rats

|  | $V_D (\mu Lg^{-1})$ | | | [$^3$H]-cIgG $V_D$ |
|---|---|---|---|---|
|  | [$^3$H]-BSA | [$^{125}$I]-cIgG | [$^3$H]-cIgG | [$^3$H]-BSA $V_D$ |
| Muscle | 42 ± 1 | 64 ± 3 | 202 ± 13 | 4.8 |
| Heart | 193 ± 4 | 227 ± 5 | 525 ± 92 | 2.7 |
| Fat | 60 ± 15 | 76 ± 19 | 139 ± 19 | 2.3 |
| Testis | 129 ± 13 | 232 ± 18 | 128 ± 18 | 1.0 |

Data are mean ± S.E. (n = 3 rats).

In general, the organ $V_o$ values for [$^3$H]-cationized IgG were several-fold above the organ $V_o$ values for [$^{125}$I]-cationized IgG. Since the formation of [$^{125}$I]-cationized IgG an oxidative process while the tritiation of IgG is a reductive procedure, it is apparent that the oxidized form [$^{125}$I]-cationized IgG) binds serum factors that inhibit the uptake of [$^{125}$I]-cationized IgG. This conclusion is supported by evidence that serum factors may bind oxidized forms of [$^{125}$I]-cationized BSA or [$^{125}$I]-cationized human albumin. (13)

FIG. 1 plots the serum radioactivity (DPM/mL/%injected) of [$^3$H]-native albumin or [$^3$H]-cationized IgG versus time after a single intravenous injection of the isotope. Only the TCA precipitable counts indicated in Table were plotted in the decay curves. The [$^3$H]-albumin data were fit — to a monoexponential function while the [$^3$H]-cationized IgG data were fit to a biexponential function. Following initial rapid clearance from blood, the rate of egress of cationized IgG is relatively slow.

The initial rapid rate of cationized IgG clearance appears to be due to rapid uptake of the IgG by liver and spleen. However, these organs have a limited number of binding sites for the cationized IgG that the clearance by liver and spleen reaches a maximum value within 5 minutes after administration. Owing to this rapid saturation, subsequent clearance of cationized IgG from blood is relatively slow, and this maintenance of a relatively constant blood concentration throughout the experimental period allows for the progressive uptake of the cationized IgG by other organs. Were it not for the limited number of binding sites for cationized IgG in liver and spleen, the rate of clearance of this protein from blood might be extremely rapid and it would be difficult to maintain a relatively constant blood level of the antibody for availability to other organs. This characteristic of cationized antibodies allows them to be present at the targeted organ in sufficient quantity for effective diagnostic or therapeutic purposes.

EXAMPLE 2

Clearance of [$^3$H]-cationized IgG and [$^{125}$I-BSA following a single intravenous injection in a primate An 0.5 mL aliquot of the same physiologic buffer as example 1 containing 500 microCi of [$^3$H]-cationized IgG and 50 microCi of [$^{125}$I]-BSA was rapidly injected into a femoral vein of an adult, male anesthetized monkey. At different times up to 60 minutes, approximately 0.3 mL aliquot of blood were removed from the ipsilateral femoral artery. After 60 minutes, the monkey was sacrificed and the organs were removed. Samples were processed for double isotope liquid scintillation counting and TCA precipitability as described above. Clearance and volume of distribution calculations were performed as described above.

Table 3 tabulates the integrated $V_D$ of [$^3$H]-cationized immunoglobulin G(cIgG) and [$^{125}$I]-bovine serum albumin (BSA) 60 minutes after a single intravenous injection in the Cynomologous Monkey. In general, the monkey $V_D$ values for native BSA at 60 minutes are comparable to $V_D$ values in the rat. Additionally, the uptake of cationized IgG by organs is substantially increased over BSA. Although the cationized IgG organ uptake in the primate was increased over that of the organ uptake of native bovine albumin, the enhanced uptake is relatively modest since the primate experiment was restricted to organ measurements at a time period of only 60 minutes following the intravenous injection. Owing to the relatively slow second phase of clearance of the cationized IgG from the primate blood (see below), there is a linear increase in the volume of distribution of the cationized IgG by many organs in the primate, proportional to the duration following the intravenous injection of cationized antibody, similarly to that observed for the rat (FIG. 2).

TABLE 3

Integrated Volume of Distribution ($V_D$) of [$^3$H]-Cationized Immunoglobulin G (cIgG) and [$^{125}$I]-Bovine Serum Albumin (BSA) 60 Minutes After a Single Intravenous Injection in a Cynomologous Monkey

| Organ | $V_D (\mu Lg^{-1})$ | | cIgG $V_D$ |
|---|---|---|---|
|  | BSA | cIgG | BSA $V_D$ |
| Liver | 350 ± 22 | 2537 ± 499 | 7.2 |
| Spleen | 387 ± 8 | 2400 ± 216 | 6.2 |
| Kidney | 312 ± 2 | 1143 ± 23 | 3.7 |
| Muscle | 14 ± 1 | 31 ± 2 | 2.2 |
| White matter | 7.2 ± 0.6 | 15 ± 1 | 2.1 |
| Fat | 19 ± 4 | 31 ± 4 | 1.6 |
| Heart | 128 ± 4 | 177 ± 10 | 1.4 |
| Lung | 439 ± 11 | 590 ± 17 | 1.3 |
| Gray matter | 18 ± 1 | 22 ± 1 | 1.2 |
| Intestine | 100 ± 7 | 118 ± 12 | 1.2 |
| Testis | 164 ± 4 | 154 ± 3 | 0.94 |
| Choroid Plexus | 301 | 279 | 0.93 |

Data are means ± S.E. (n = 3 samples from one monkey).

Figure 3:
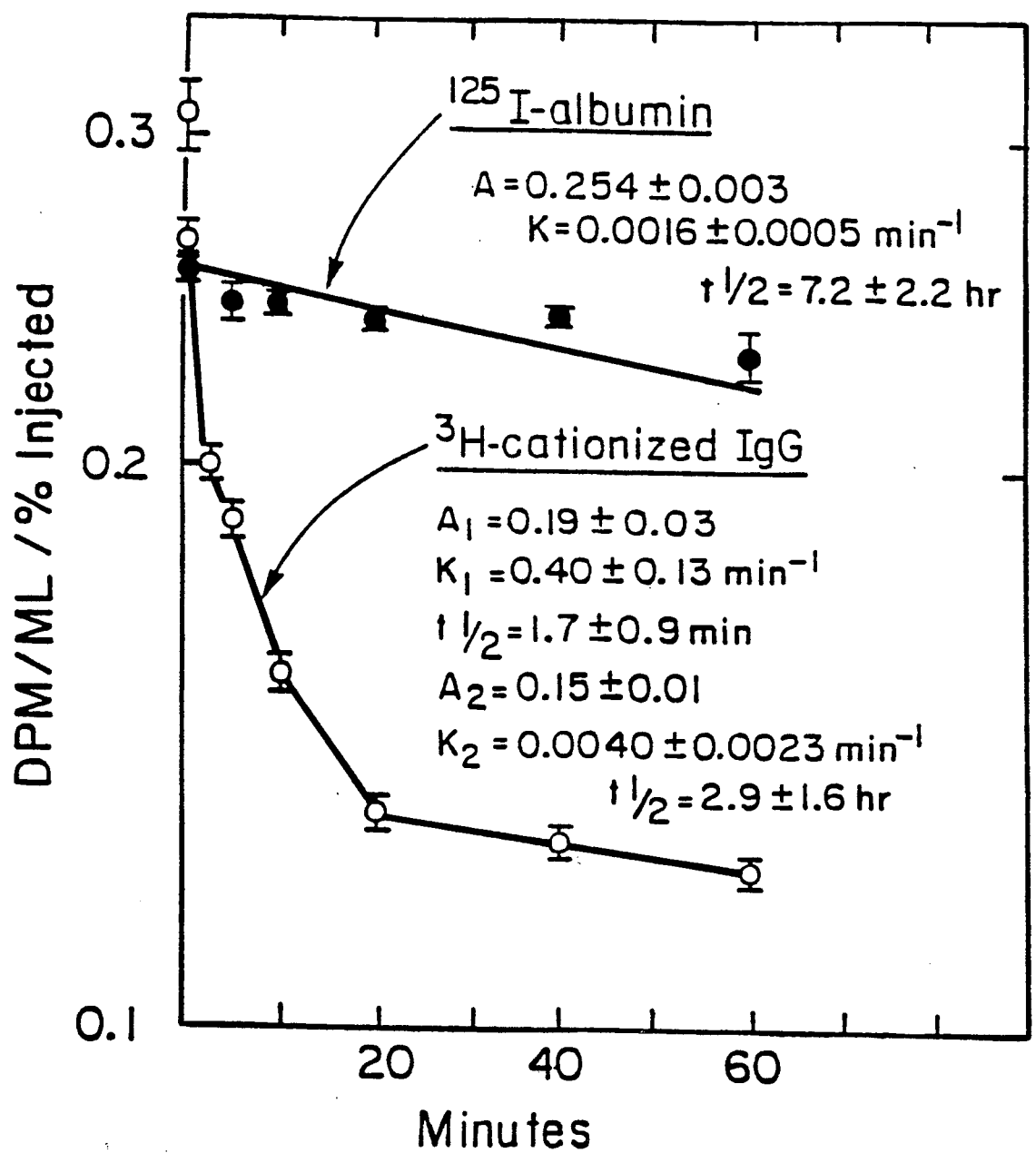
FIG. 3 is a plot of serum [$^{125}$I]-bovine serum albumin radioactivity and [$^3$H]-cationized IgG radioactivity over a 60 minute period after a single intravenous injection of isotope in the anesthetized cynomologous monkey.

FIG. 3 illustrates the decay in serum [$^{125}$I]-native BSA and [$^3$H]-cationized IgG radioactivity following a single intravenous injection in a Macaca irus monkey. As indicated in FIG. 3, the total DPMs injected at zero time for the labelled BSA (0.254 DPM/ML/% injected) is about 14 fold lower than that for labelled BSA in the rat (3.5 DPM/ML/% injected, FIG. 1). Since the weight of the primate is approximately 14 fold greater than the weight of the rat it is likely that the difference is due to the larger primate blood volume. It is clear from the rat and primate experiments that the cationization procedure in accordance with the present invention results in markedly increased rates of uptake of the IgG by organs after cationization of antibodies.

The data shown in FIGS. 1 and 3 illustrate the highly favorable pharmacokinetics of [$^3$H]-cationized IgG clearance by organs. Owing to the rapid saturation of uptake sites in liver and spleen, there is a prolonged slow second phase of clearance of [$^3$H]-cationized IgG from blood. The maintenance of this prolonged slow phase of clearance from blood allows for progressive and linear increase of the cationized IgG by a number of different organs. The relatively long half-time of cationized IgG (e.g., 3.0 ±1.0 hours in rats or 2.9 ±1.6 hours in a primate) indicates that the cationized IgG pharmaceutic need not be administered continuously, but could be administered on a once, twice, or three times a day basis.

Having thus described exemplary embodiments of the present invention, it should be noted by those skilled in the art that the within disclosures are exemplary only and that various other alternatives, adaptations and modifications may be made within the scope of the present invention. Accordingly the present invention is not limited to the specific embodiments as illustrated herein, but is only limited by the following claims.

REFERENCES

1. Reynoso, G., Keane, M., and Reynoso, M. A. (1985): Monoclonal carcinoembryyonic antigen antibodies. In: Monoclonal Antibodies in Cancer (Sell, S. and Reisfeld, R. A., eds.). Humana Press, Clifton, New Jersey, pp. 19-40.

2. Harden E. A., Palker, T. J., and Haynes, B. F. (1985): Monoclonal antibodies. Probes for study of malignant T cells. In: Monoclonal Antibodies in Cancer (Sell, S. and Reisfeld, R. A., eds.). Humana Press, Clifton, New Jersey, pp. 121-145.

3. Reisfeld, R. A. (1985): Monoclonal antibodies as probes for the molecular structure and biological function of melanoma-associated antigens. In: Monoclonal Antibodies in Cancer (Sell, S. and Reisfeld, R. A., eds.). Humana Press, Clifton, New Jersey, pp. 205-228.

4. Rittmann, L. S., Sobol, R. E., Astarita, R. W., and Martinis, J. (1985): Monoclonal antibodies to human small-cell lung cancer. In: Monoclonal Antibodies: Diagnostic and Therapeutic Use in Tumor and Transplantation (Chatterjee, S. M., ed.). PSG Publishing Company, Inc., Littleton, Massachusetts, pp. 73-83.

Mulshine, J. L., Cuttitta, F., and Minna, J. D. (1985): Lung cancer markers as detected by monoclonal antibodies. In: Monoclonal Antibodies in Cancer (Sell, S. and Reisfeld, R. A., eds.). Humana Press, Clifton, New Jersey, pp. 229-246.

5. Chu, T. M. (1985): Monoclonal antibodies to human prostate cancer-related antigens. In: Monoclonal Antibodies to Cancer (Sell, S. and Reisfeld., R.A., eds.). Humana Press, Clifton, New Jersey, pp. 309-324.

Raynor, R. H., Mohanakumar, T., Monclure, C. W., and Hazra, T. A. (1985): Monoclonal antibodies to human prostate tissued. In: Monoclonal-Antibodies (Chatterjee, S. M., ed.). PSG Publishing Company, Inc., Littleton, Massachusetts, pp. 155-161.

6. Schlom, J., Greiner, J., Hand, P. H., Colcher, D., Inghiram, G., Weeks, M., Pestka, S., Fisher, P. B., Noguchi, P., and Kufe, D. (1985): Human breast cancer markers defined by monoclonal antibodies. In: Monoclonal Antibodies in Cancer (Sell, S. and Reisfeld, R.A., eds.). Humana Press, Clifton, New Jersey, pp. 247-278.

7. Bander, N. H. and Cordon-Cardo, C. (1985): Monoclonal antibodies to renal cancer markers. In: Monoclonal Antibodies in Cancer (Sell, S. and Reisfeld, R.A., eds.). Humana Press, Clifton, New Jersey, pp. 325-338.

8. Drew, S. I., Terasaki, P. I., Johnson, C., Chia, D., Wakisaka, A., Hardiwidjaja, S., Cicciarelli, J., Takasugi, M., Kaszubowski, P., Quinlan, T., Izuka, T., and Hirata, A. (1985): Phase I study of high-dose serotherapy with cytotoxic monoclonal antibodies in patients with gastrointestinal malignancies. In: Monoclonal Antibodies (Chatterjee, S. N., ed.). PSG Publishing Company, Inc., Littleton, Massachusetts, pp. 127-136.

9. Hollingsworth, M. A. and Metzgar, R. S. (1985): Antigens of normal and malignant human exocrine pancreatic cells. In: Monoclonal Antibodies in Cancer (Sell, S. and Reisfeld, R.A., eds.). Humana Press, Clifton, New Jersey, pp. 279-308.

10. Hoare, Koshland. A Method for the Quantitative Modification of Estimation of Carboxylic Acid Groups in Proteins. (1967) J Biol. Chem. 342:2447-2453.

11. Triguero, D., Buciak, J. B., Yang, J., Pardridge, W. M. Blood Brain Barrier Transport of Cationized Immunoglobulin G. Proc. Natl. Acad. Sci., U.S.A. 86: 471-4765, 1989.

12. Pardridge, W. M., Eisenberg, J., and Cefalu, W. T. Absence of albumin receptor on brain capillaries in vivo or in vitro. Am. J. Physio., 249: E264-E267, 1985.

13. Bergmann, P., Vizet, A., Sennesael, J., Beauwens, R., and Snauwaert, J. Bonding of cationized albumin to red cells. In: The Pathogenicity of Cationic Proteins (ed. P. P. Lambert, P. Bergmann, and R. Beauwens), Raven Press, New York, pp. 29-39, 1983.

I claim:

1. A method for increasing the transcytosis of an antibody across the microvascular barrier and into the interstitial fluid of mammalian non-central nervous system tissues or organs, said method comprising the steps of:

treating said antibody with a sufficient amount of a cationization agent to increase the isoelectric point of said antibody by between about 1 to about 7 pH units to produce a cationized antibody having an isoelectric point which is less than about pH 11.5;

mixing said cationized antibody with a pharmaceutically acceptable carrier to provide a cationized antibody composition; and administering said cationized antibody composition to a mammal wherein the transcytosis of said cationized antibody across the microvascular barrier and into the interstitial fluid of said organs is increased over the transcytosis of said antibody across said microvascular barrier.

2. A method according to claim 1 wherein said antibody has a molecular weight greater than 20,000 Daltons.

3. A method according to claim 1 wherein said antibody is a monoclonal antibody.

4. A method according to claim 1 wherein said antibody is IgG.

5. A method according to claim 1 wherein said antibody is IgM.

6. A method according to claim 3 wherein said antibody is labeled with a detectable radionuclide.

7. A method according to claim 3 wherein said antibody is labeled with a detectable paramagnetic conjugate.

8. A method according to claim 3 wherein said antibody is labeled with a pharmaceutically active drug.

9. The method according to claim 3 wherein said monoclonal antibody is specific for an organ.

10. The method according to claim 3 wherein said non-central nervous system tissues or organs include one or more organ selected from the group consisting of spleen, liver, kidney, lung, small intestine, heart, skeletal muscle, lymphoids, skin, prostate, pancreas, breast, esophagus, and fat.

11. The method according to claim 3 wherein said monoclonal antibody is selected from the group consisting of antibodies to carcinoembryonic antigen, T-lymphocyte receptors, melanoma antigens, lung cancer antigens, prostate cancer antigens, human breast cancer antigens.

12. The method according to claim 3 wherein said cationization agent is an amine cationization agent.

13. The method according to claim 12 wherein said amine cationization agent is hexamethylenediamine.

* * * * *